United States Patent [19]

Weimer et al.

[11] Patent Number: 5,935,370
[45] Date of Patent: Aug. 10, 1999

[54] METHOD FOR LAMINATING A VIRAL BARRIER MICROPOROUS MEMBRANE TO A NONWOVEN WEB TO PREVENT TRANSMISSION OF VIRAL PATHOGENS

[75] Inventors: William K. Weimer, Woodbury; Gretchen E. Keenan, Edina; Robert J. Kinney, Woodbury; James S. Mrozinski, Oakdale; Philip D. Radovanovic, Minneapolis, all of Minn.

[73] Assignee: #M Innovative Properties Company Minnesota Mining and Manufacturing Co., St. Paul, Minn.

[21] Appl. No.: 08/545,556

[22] Filed: Oct. 19, 1995

Related U.S. Application Data

[60] Division of application No. 08/384,079, Feb. 6, 1995, abandoned, which is a continuation-in-part of application No. 08/105,430, Aug. 10, 1993, abandoned, which is a continuation-in-part of application No. 07/962,416, Oct. 16, 1992, abandoned, which is a continuation-in-part of application No. 07/779,014, Oct. 18, 1991, abandoned.

[51] Int. Cl.⁶ ........................................................ B32B 31/00
[52] U.S. Cl. ............................................. 156/290; 428/198
[58] Field of Search ............................. 156/290; 428/198

[56] References Cited

U.S. PATENT DOCUMENTS

| | | |
|---|---|---|
| 3,341,497 | 9/1967 | Sherman et al. . |
| 3,426,754 | 2/1969 | Bierenbaum et al. . |
| 3,801,404 | 4/1974 | Druin et al. . |
| 3,801,692 | 4/1974 | Zimmerman . |
| 3,839,240 | 10/1974 | Zimmerman . |
| 3,843,761 | 10/1974 | Bierenbaum et al. . |
| 3,844,865 | 10/1974 | Elton et al. . |
| 3,856,005 | 12/1974 | Sislian . |
| 3,870,593 | 3/1975 | Elton et al. . |
| 3,870,748 | 3/1975 | Katsushima et al. . |
| 3,911,499 | 10/1975 | Benevento et al. . |
| 3,923,715 | 12/1975 | Dettre et al. . |
| 3,953,566 | 4/1976 | Gore . |
| 3,962,153 | 6/1976 | Gore . |
| 4,041,203 | 8/1977 | Brock et al. . |
| 4,084,059 | 4/1978 | Katsushima et al. . |
| 4,096,227 | 6/1978 | Gore . |
| 4,194,041 | 3/1980 | Gore et al. . |
| 4,196,245 | 4/1980 | Kitson et al. . |
| 4,270,658 | 6/1981 | Schuster . |
| 4,347,844 | 9/1982 | Ohki et al. . |
| 4,374,888 | 2/1983 | Bornslaeger . |
| 4,374,889 | 2/1983 | Arens . |
| 4,379,192 | 4/1983 | Wahlquist et al. . |
| 4,419,993 | 12/1983 | Petersen . |
| 4,433,026 | 2/1984 | Molde . |
| 4,443,511 | 4/1984 | Worden et al. . |
| 4,515,841 | 5/1985 | Dyke . |
| 4,519,909 | 5/1985 | Castro . |
| 4,539,256 | 9/1985 | Shipman . |
| 4,542,771 | 9/1985 | Payet et al. . |
| 4,555,293 | 11/1985 | French . |
| 4,609,584 | 9/1986 | Cutler et al. . |
| 4,613,544 | 9/1986 | Burleigh . |
| 4,644,586 | 2/1987 | Padgett . |
| 4,705,812 | 11/1987 | Ito et al. . |
| 4,726,989 | 2/1988 | Mrozinski . |
| 4,777,073 | 10/1988 | Sheth . |
| 4,824,718 | 4/1989 | Hwang . |
| 4,828,556 | 5/1989 | Braun et al. . |
| 4,845,779 | 7/1989 | Wheeler et al. . |
| 4,847,142 | 7/1989 | Twilley et al. . |

(List continued on next page.)

FOREIGN PATENT DOCUMENTS

| | | |
|---|---|---|
| 0 505 027 A1 | of 0000 | European Pat. Off. . |
| 260 011 A2 | 3/1988 | European Pat. Off. . |
| H.2-212527 | of 0000 | Japan . |
| S.60-142860 | of 0000 | Japan . |
| S.64-22305 | of 0000 | Japan . |
| 63-276533 | 11/1988 | Japan . |
| H.1-305001 | 12/1989 | Japan . |
| 2232905 | of 0000 | United Kingdom . |
| 2149343 | 6/1985 | United Kingdom . |
| WO 93/07914 | 4/1993 | WIPO . |
| WO 93/08019 | 4/1993 | WIPO . |
| WO 95/03172 | 2/1995 | WIPO . |
| WO 95/16562 | 6/1995 | WIPO . |
| WO 95/23696 | 9/1995 | WIPO . |
| WO 96/09165 | 3/1996 | WIPO . |
| WO 96/16562 | 6/1996 | WIPO . |
| WO 96/31345 | 10/1996 | WIPO . |

OTHER PUBLICATIONS

"Emergency Standard Test Method for Resistance of Protective Clothing Materials to Synthetic Blood", ASTM Test Designation ES 21–92, pp. 1–4 (1992).

"Emergency Standard Test Method for Resistance of Protective Clothing Materials to Penetration by Blood–Borne Pathogens Using Viral Penetration as a Test System", ASTM Test Designation ES 22–92, pp. 1–7 (1992).

D.J. Bucheck, "Comfortable clothes through chemistry", *Chemtech*, 21, 142–147 (1991).

E.A. McCullough et al., "Liquid Barrier Properties of Nin Surgical Gown Fabrics", *INDA JNR*, 3, 14–20 (1991).

A.L. Panlilio et al., "Blood Contacts During Surgical Procedures", *JAMA*, 265, 1533–1537 (1991).

Plenkiewicz et al., "Synthetic Uility of 3–(Perfluoro–1, 1Dimethyl–1–Propene. Part II. Synthesis of New 2–Hydroxy–3–(perfluoro–alkyl)Propyl–Amines," *Journal of Fluorine Chemistry*, vol. 45, pp. 389–400 (1989).

Katritzky et al., "Design and Synthesis of Novel Fluorinated Surfactants for Hydrocarbon Subphases," *Langmuir*, vol. 4, No. 3, pp. 732–735 (1988).

*Primary Examiner*—John J. Gallagher
*Attorney, Agent, or Firm*—Gary L. Griswold; Robert W. Sprague; William J. Bond

[57] ABSTRACT

The invention discloses a method of preventing transmission of viral pathogens between a source of viral pathogens and a target of said viral pathogens comprising positioning between said source and said target a microporous membrane material comprising (1) a thermoplastic polymer or polytetrafluoroethylene and (2) a water- and oil-repellent fluorochemical compound which provides said membrane with oleophobic, hydrophobic and viral barrier properties.

9 Claims, No Drawings

U.S. PATENT DOCUMENTS

| | | |
|---|---|---|
| 4,863,792 | 9/1989 | Mrozinski . |
| 4,867,881 | 9/1989 | Kinzer . |
| 4,877,679 | 10/1989 | Leatherman et al. . |
| 4,898,761 | 2/1990 | Dunaway et al. . |
| 4,920,960 | 5/1990 | Hubbard et al. . |
| 4,929,303 | 5/1990 | Sheth . |
| 4,937,115 | 6/1990 | Leatherman . |
| 4,954,256 | 9/1990 | Degen et al. . |
| 4,961,985 | 10/1990 | Henn et al. . |
| 4,975,469 | 12/1990 | Jacoby et al. . |
| 4,976,274 | 12/1990 | Hanssen . |
| 4,983,450 | 1/1991 | Yanagihara et al. . |
| 5,013,439 | 5/1991 | Fisher et al. . |
| 5,017,292 | 5/1991 | DiLeo et al. . |
| 5,025,052 | 6/1991 | Crater et al. .......................... 524/104 |
| 5,026,591 | 6/1991 | Henn et al. .......................... 428/198 |
| 5,032,450 | 7/1991 | Rechlicz et al. . |
| 5,043,209 | 8/1991 | Boisse et al. . |
| 5,045,133 | 9/1991 | DaPonte et al. . |
| 5,055,338 | 10/1991 | Sheth et al. . |
| 5,110,506 | 5/1992 | Ciallella . |
| 5,114,787 | 5/1992 | Chaplin et al. . |
| 5,116,650 | 5/1992 | Bowser . |
| 5,120,594 | 6/1992 | Mrozinski . |
| 5,126,189 | 6/1992 | Tanny et al. . |
| 5,134,017 | 7/1992 | Baldwin et al. . |
| 5,156,780 | 10/1992 | Kenigsberg et al. . |
| 5,169,712 | 12/1992 | Tapp . |
| 5,176,953 | 1/1993 | Jacoby et al. . |
| 5,178,932 | 1/1993 | Perkins et al. . |
| 5,187,005 | 2/1993 | Stahle et al. . |
| 5,208,098 | 5/1993 | Stover . |
| 5,260,360 | 11/1993 | Mrozinski et al. . |
| 5,264,276 | 11/1993 | McGregor et al. . |
| 5,308,691 | 5/1994 | Lim et al. . |
| 5,317,035 | 5/1994 | Jacoby et al. . |
| 5,352,108 | 10/1994 | Kagawa et al. . |
| 5,352,513 | 10/1994 | Mrozinski et al. . |
| 5,393,603 | 2/1995 | Toyoda et al. . |
| 5,409,761 | 4/1995 | Langley .................................. 428/198 |
| 5,532,053 | 7/1996 | Mueller . |
| 5,560,974 | 10/1996 | Langley . |

5,935,370

METHOD FOR LAMINATING A VIRAL BARRIER MICROPOROUS MEMBRANE TO A NONWOVEN WEB TO PREVENT TRANSMISSION OF VIRAL PATHOGENS

This application is a division of application Ser. No. 08/384,079 filed Feb. 6, 1995, now abandoned, which is a continuation-in-part of application Ser. No. 08/105,430, filed Aug. 10, 1993 abandoned, which is a continuation-in-part of application Ser. No. 07/962,416, filed Oct. 16, 1992 abandoned, which is a continuation-in-part of application Ser. No. 07/779,014 filed Oct. 18, 1991 abandoned.

TECHNICAL FIELD

This invention relates to a method for preventing transmissions of viral pathogens using a microporous membrane which is breathable, liquid repellent, and a viral barrier. The membrane or membrane laminated to a fabric can be used as a surgical gown, drape, mask, gloves, sterile wraps, wound dressings, waste disposal bag or other products requiring viral barrier properties combined with breathability.

BACKGROUND OF THE INVENTION

Surgical gowns, drapes and the like protect surgically prepared areas of the skin from contamination and also protect surgeons and nurses against contamination through contact with unprepared or contaminated areas of patient's skin. In addition, surgical gowns and drapes should present a sterile barrier to protect patients from contamination through contact with the surgeon.

Liquid repellency of the gown or drape is recognized as an important property in assuring that the gown or drape protects and acts as a barrier to the passage of bacteria or viruses carried in liquids. Body liquids and other liquids can permeate through the surgical gown or drape lacking liquid repellency properties. Thus, bacteria and viruses, such as the human immunodeficiency virus and hepatitis B virus, which may be present on the surface of the gown or drape can be transported through the gown to the patient or the operating room personnel.

In addition to being liquid repellent and a bacteria and viral barrier, hospital gowns and drapes desirably present a non-glare outer surface, are nonlinting, possess antistatic characteristics, and, not least importantly, are comfortable to wear.

It has been widely recognized that garments must be "breathable" to be comfortable. While it is not necessary, although preferable, that air pass through the garment for it to be comfortable, it is essential that water vapor from perspiration be transmitted from inside to outside so that a natural evaporative cooling effect can be achieved. If a continuous film of hydrophilic material is exposed to air containing a high concentration of water vapor on one side of the film, and to air containing a lower concentration of water vapor on the other side, the side of the film exposed to the higher water vapor concentration will absorb water molecules which diffuse through the film and are desorbed or evaporated on the side exposed to the lower water vapor concentration. Thus, in a continuous film of hydrophilic material, water vapor is effectively transported through the film on a molecule by molecule basis. This property is known as moisture vapor transmission. Generally, in microporous films water vapor is also transported by the diffusion of water vapor in the air which is able to permeate the membrane.

One type of commonly used protective clothing is made from nonwoven substrate calendared at high temperature and pressure. While having reasonable properties for protection, garments constructed of this material are known to be very uncomfortable due to their inherent low moisture vapor transmission and low air permeability characteristics, i.e., their low breathability. Various attempts have been made to improve breathability of this nonwoven material. These efforts, however, frequently result in a more open structure of the nonwoven material and thus also simultaneously lower its protection value. Coatings on polyolefin nonwovens have been employed to afford greater barrier protection to the 'open' base structure of the nonwoven. However, the already inherently low moisture transmission and air permeability characteristics of the nonwoven material are even further reduced, simultaneously reducing the comfort of garments made by use of this technology.

Protective clothing in hospital operating rooms has been made of spun-laced nonwovens of polyester and wood pulp fibers, heavily treated with a water-repellent. Here, again, a compromise in properties must be reached. Greater comfort sacrifices maximum microorganism barrier protection and greater barrier protection lowers comfort. For instance, where hospital operating room gown products require superior protection from microorganisms, a dense, nonporous polyethylene film is usually laminated to the nonwoven. But, while achieving good barrier characteristics, moisture vapor transmission is substantially eliminated.

As seen from the foregoing, protection properties and comfort properties are traded off with one another. The present invention allows for both desirably good barrier protection characteristics while simultaneously achieving excellent moisture vapor transmitting characteristics, i.e. providing both protection and comfort.

U.S. Pat. No. 4,961,985 (Henn et al.) describes a coated product for use as a fabric for protective clothing. The product is made of a substrate and a coating comprised of a microporous scaffold material having a high void volume and open, interconnecting void microstructure, at least partially filled with a layer of a selected polyurethane. The product has viral barrier properties.

U.S. Pat. No. 5,017,292 (DiLeo et al.) describes a particular asymmetric composite membrane structure having skin possessing ultrafiltration separation properties, a porous substrate and a porous intermediate zone that is particularly useful for selectively isolating virus from a protein-containing solution.

Japanese Laid-Open (Kokai) Patent Application S.60-142860 (Kawase et al.) describes a method of removing viruses in water or a water solution by filtering through a porous polyolefin membrane having micropores with an average diameter of 0.05–0.30 mm, a pore rate of 30–90 (v/v) %, a thickness of 5–100 mm and air filtration velocity of $5$–$30 \times 10^4$ l/m$^2$ hr 0.5 atm at a between-membrane pressure difference of less than 2 kg/cm$^2$.

Japanese Laid-Open (Kokai) Patent Application H. 1-305001 (Mitsutani) describes a method of preserving bulbs using a material which allows oxygen to pass through but prevents viruses from reaching the bulbs. The material is a film described as a porous, hydrophilic polyolefin, polyvinyl alcohol, cellulose acetate, regenerated cellulose, polypropylene, polyethylene, polyethylene copolymer, cellulose mixed ester resin and fluoride resin. The material may also be a solution that can be coated onto the bulb. This material should be water soluble, allow oxygen to pass through, but stop viruses. Examples of this material are cellulose acetate phthalate, methyl methacrylate methacrylic acid, polymer synthetic products, cellulose, and natural products.

Japanese Laid-Open (Kokai) Patent Application H2-212527 (Matsumoto) describes a method for making a porous filtration membrane by exposing a film to high energy particles, chemically etching the film to make uniform pore diameters, and graft polymerizing a hydrophilic monomer such as acrylic acid onto the porous film. The polymer for the film is selected from polyethylene, polypropylene, ethylene-alpha-olefin copolymer such as ethylene-propylene copolymer and polyvinylidene fluoride. The porous membrane described in this application can be used in the water system for separation of bacteria and viruses.

Japanese Laid-Open (Kokai) Patent Application S.64-22305 (Shiro) describes porous polypropylene fibers and the pathogenic agent filtering apparatus using these fibers. The apparatus can remove pathogenic agents (bacteria and viruses) contained in the serum from the blood of germ carriers. The hollow fiber is formed by special drawing and stretching conditions. The hollow fiber is characterized in that the pore shape is extremely uniform and the pore diameter distribution is narrow. The pore diameter is on the average of 50–250 nanometers.

U.S. Pat. No. 4,194,041 (Gore et al.) is representative of a number of patents which describe coatings or laminates purported to provide waterproof articles which do not leak when touched and are breathable. This patent describes a layered article for use in waterproof garments or tents comprising at least two layers: an interior, continuous hydrophilic layer that readily allows water vapor to diffuse therethrough, prevents the transport of surface active agents and contaminating substances such as those found in perspiration, and is substantially resistant to pressure induced flow of liquid water, and a hydrophobic layer that permits the transmission of water vapor and provides thermal insulating properties even when exposed to rain. The hydrophobic layer is preferably waterproof microporous tetrafluoroethylene (PTFE) or polypropylene, which permits the passage of moisture vapor through the pores thereof. The hydrophilic layer transfers moisture vapor therethrough whereupon it passes through the porous hydrophobic layer. Various means of joining the layers are suggested including the application of hydraulic pressure to force the hydrophilic polymer to penetrate into the surface void spaces of the hydrophobic layer.

U.S. Pat. No. 4,443,511 (Worden et al.) discloses a layered waterproof, breathable and stretchable article for use in, for example, material for protective articles. Also disclosed is a waterproof and breathable elastomeric polytetrafluoroethylene layered article bonded to a stretch fabric. The water proof and breathable elastomeric polytetrafluoroethylene layered article bonded to a stretch fabric is described as durable and possessing a moisture vapor transmission rate exceeding 1000 gms/m$^2$ day.

U.S. Pat. No. 4,613,544 (Burleigh) describes a waterproof, moisture vapor permeable unitary sheet material comprising a microporous polymeric matrix having pores comprising continuous passages extending through its thickness and opening into the opposite surfaces thereof, the passages being sufficiently filled with a moisture vapor permeable, water impermeable, hydrophilic material to prevent the passage of water and other liquids through the unitary sheet material while readily permitting moisture vapor transmission therethrough rendering the sheet material breathable. The unitary sheet is made by causing a liquid composition comprising the hydrophilic material or precursor thereof to flow into the pores of the matrix, then causing the conversion thereof to solid hydrophilic material.

While these materials alleviate some of the problems known to the art, many require lamination to protect the water repellent, moisture vapor permeable material they use in their constructions while others require void filling which can lower the moisture vapor transmission rate of the material and decrease its ability to heat seal. Joining of multiple pieces of these materials in a three dimensional garment presents additional problems in that most of these materials are not readily joined together by any means other than sewing which creates needle holes that must be subsequently sealed with seaming tapes or alternative filling techniques to provide a totally waterproof garment. Also, due to the dense nature of the hydrophilic layer, many of these materials are minimally permeable to air.

U.S. Pat. No. 5,025,052 (Crater et al.) describes fluorochemical oxazolidinone compositions and their use for oil and water repellency in films, fibers, and non-woven webs.

U.S. Pat. No. 4,539,256 (Shipman) discloses a microporous sheet material formed by liquid-solid phase separation of a crystallizable thermoplastic polymer with a compound which is miscible with the thermoplastic polymer at the melting temperature of the polymer but phase separates on cooling at or below the crystallization temperature of the polymer.

U.S. Pat. No. 4,726,989 (Mrozinski) discloses a microporous material similar to that of Shipman but which also incorporates a nucleating agent.

U.S. Pat. No. 4,867,881 (Kinzer) discloses an oriented microporous film formed by liquid-liquid phase separation of a crystalline thermoplastic polymer and a compatible liquid.

The present invention relates to a method of preventing transmission of viral pathogens between a source of viral pathogens and a target of said viral pathogens comprising positioning between said source and said target a microporous membrane material comprising (1) a thermoplastic polymer or polytetrafluoroethylene and (2) a water- and oil-repellent fluorochemical compound which provides said membrane with oleophobic, hydrophobic and viral barrier properties. The fluorochemical compound can be introduced as a melt additive during the membrane preparation or as a topical treatment after the membrane is made. The membrane material is moisture vapor, air permeable and sweat contamination resistant. The membrane material is also heat sealable when made using a thermoplastic polymer.

In a preferred embodiment, the membrane comprises (1) a crystallized olefin polymer, and, disposed within the pores a processing compound which is miscible with the olefin polymer at the melting point of the polymer but phase separates on cooling to or below the crystallization temperature of the polymer and (2) a fluorochemical oxazolidinone compound, a fluorochemical aminoalcohol compound, an amorphous fluoropolymer, a fluoroacrylate polymer, a fluorochemical piperazine, a fluorochemical acrylic ester or a blend thereof.

In another preferred embodiment of the invention, the microporous membrane comprises (1) a polyolefin resin or a blend of polyolefin resins (2) finely divided inorganic filler material having a melting point above the polyolefin degradation temperature(s) and (3) a fluorochemical compound which provides the membrane with viral barrier properties, the membrane being oriented in at least one direction. Generally, the fluorochemical compound is a water- and oil-repellent fluorochemical compound. Preferred fluorochemical compounds include fluorochemical oxazolidinones, fluorochemical aminoalcohols, amorphous fluoropolymers, fluoroacrylate polymers, fluorochemical piperazines, fluorochemical stearates and blends thereof.

The present invention further provides a microporous membrane material and articles such as surgical gowns, drapes, masks, gloves, sterile wraps, wound dressings and waste disposal bags for containment of virally contaminated materials, comprising (1) a thermoplastic polymer or polytetrafluoroethylene and (2) a water- and oil-repellent fluorochemical compound which provides said membrane with oleophobic, hydrophobic and viral barrier properties. The articles may be disposable or reusable.

The microporous membrane materials useful in the present invention retain their viral barrier, liquid repellency and moisture vapor and air permeability properties for extended periods even in garment and surgical drape applications which expose the membrane materials to perspiration residues which are known to contaminate and ultimately destroy repellency properties of conventional liquid repellent, moisture vapor permeable materials. Surprisingly, the materials useful in the invention prepared by incorporating the fluorochemical compound as a melt additive retain this contamination resistance to perspiration despite the presence of the processing compound, an oleophilic material. Further, the microporous membrane materials useful in the invention repel mineral oil even when they contain mineral oil. The microporous membrane materials useful in the present invention also possess excellent hand and drape properties.

DETAILED DESCRIPTION

The viral barrier, liquid repellent, moisture vapor and air permeable, microporous membrane materials useful in the present invention repel aqueous based fluids as well as a variety of other liquids, such as perspiration which contains oil-based components, and prevent penetration of the liquids through the thin (5 to 250 microns) membrane, even when the liquid is propelled against the membrane material. The microporous membrane materials, while water repellent, also have very high moisture vapor permeabilities coupled with significant air permeability properties.

Garments fabricated from the microporous membrane materials useful in the present invention allow for the transfer of moisture vapor resulting from perspiration through the garment at a rate sufficient to maintain the skin of the wearer in a reasonably dry state under normal use conditions. The microporous membrane materials useful in the present invention differ from prior art single layer microporous liquid repellent, moisture vapor permeable materials in that they are not subject to contamination by perspiration residues which reduce and ultimately destroy the repellency properties of the material. This difference allows the membrane materials useful in the present invention to be used in garment applications without a protective overlayer.

The microporous membrane materials useful in the present invention exhibit durability of their liquid repellency properties when subjected to sterilization, rubbing, touching, folding, flexing or abrasive contacts. The microporous membrane materials useful in the present invention also display oleophobic properties, resisting penetration by oils and greases and they are heat sealable when thermoplastic. The oleophobicity and heat sealing properties of the membrane materials prepared by phase separation are most surprising in that the membrane materials contain an oily, oleophilic processing compound which, a priori, one would expect, would promote wetting by other oleophilic materials and which also would inhibit heat sealing.

Transport of a liquid challenge through most porous materials or fabrics occurs because the liquid is able to wet the material. The likely route through the material is for the liquid to initially wet the surface of the material and to subsequently enter the pore openings at the surface of the material followed by a progressive wetting of and travel through the interconnected pores until finally reaching the opposite surface of the material. If the liquid has difficulty wetting the material, liquid penetration into and through the material will, for the most, be reduced. The similar phenomena occurs in the pores, where reduced wetability, in turn, reduces pore invasion. The greater the numerical difference between the liquid surface tension of the liquid and the surface energy of the porous material (the latter being lower), the less likely the liquid will wet the porous material.

The addition of a fluorochemical to the microporous membrane useful in the present invention reduces the surface energy of the membrane, thereby increasing the numerical difference between its surface energy and the surface tension of challenge liquids. A preferred class of fluorochemicals is fluorochemical oxazolidinone compounds which are normally solid at room temperature, water-insoluble, fluoroaliphatic radical-containing 2-oxazolidinone compounds which have one or more 2-oxazolidinone moieties, at least one of which has a monovalent fluoroaliphatic radical containing at least 3 fully fluorinated terminal carbon atoms bonded to the 5-position carbon atom thereof by an organic linking group. Particularly preferred is a fluorochemical oxazolidinone represented by the formula

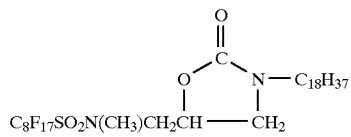

Such oxazolidinones are described, for example, in U.S. Pat. No. 5,025,052 (Crater et al.) which is incorporated herein by reference.

Another preferred class of fluorochemical compounds is fluorochemical aminoalcohol compounds. Such fluorochemical aminoalcohol compounds are disclosed, for example, in U.S. Pat. No. 3,870,748 (Katsushima et al.), U.S. Pat. No. 4,084,059 (Katsushima et al.) which are incorporated by reference herein and Plenkiewicz et al., "Synthetic Utility of 3-(Perfluoro-1,1-Dimethyl-1-Propene. Part II. Synthesis of New 2-Hydroxy-3-(Perfluoro-alkyl) Propyl-Amines", *Journal of Fluorine Chemistry* vol. 45, pp 389–400 (1989).

Additional preferred fluorochemical compounds useful for topical treatment of the microporous membrane include amorphous fluoropolymers available under the tradename TEFLON from DuPont Polymer Products, fluoroacrylate polymers which can be formed from fluoroacrylate monomers available under the tradename ZONYL from DuPont Polymer Products, fluorochemical carboxylic acid esters such as those disclosed in U.S. Pat. No. 3,923,715 (Dettre et al.) and fluorochemical acrylic copolymers such as those described in U.S. Pat. No. 3,341,497, and fluorochemical piperazines which can be prepared by reacting fluoroaliphatic radical-containing piperazine compounds such as described in Katritzky et al., "Design and Synthesis of Novel Fluorinated Surfactants for Hydrocarbon Subphases,"

*Langmuir,* vol. 4, no. 3, pp. 732–735 (1988) with, e.g., aliphatic and aromatic epoxides, halides and isocyanates.

It is also expected that additional oil and water repellent fluorochemical compositions would also provide viral barrier properties when added during extrusion at the proper extrusion conditions or when topically applied. Preferably, the fluorochemical composition is soluble in the polymer or processing compound in the molten state.

The oleophobic, hydrophobic, moisture vapor permeable, air permeable, viral barrier, heat sealable, microporous membrane materials useful in the present invention preferably comprise a polymeric microporous membrane having a matrix of pores comprising continuous passages extending through the thickness of the membrane and opening into the opposite surfaces of the membrane. The polymer used to prepare the microporous membrane useful in the present invention preferably contains a fluorochemical oxazolidinone compound or a fluorochemical aminoalcohol compound which migrates to an air interface, thereby lowering the surface energy of the faces of the membrane as well as the walls of the pores in the membrane, and enhancing the hydrophobic properties of the microporous membrane as well as rendering the microporous membrane material oleophobic.

The microporous membrane materials useful in the present invention can be tailored to have moisture vapor permeability rates over a broad range without adversely impacting their water repellencies, but it is preferable to have a moisture vapor transmission rate (MVTR) of at least 1000 $g/m^2/24$ hrs., more preferably a MVTR of at least 2000 $g/m^2/24$ hrs., and most preferably a MVTR of at least 5000 $g/m^2/24$ hrs.

"Moisture vapor permeable" is used herein to describe microporous membrane materials which readily permit the passage of water vapor through the fabric but which do not allow the passage of liquid water.

The term "water repellent" is used herein to describe microporous membrane materials which are not water wettable and are capable of preventing the passage of liquid water through the membrane material by capillary action under varying ambient atmospheric conditions, including water impinging on the surface of the membrane material.

The term "hydrophobic" is used herein to describe microporous membrane materials which are not wet by liquid water or aqueous body fluids such as blood, saliva, perspiration and urine, and which are capable of repelling and preventing the passage of liquid water through their structure.

The term "oleophobic" is used herein to describe microporous membrane materials which are not wet by oils, greases or body fluids which contain oily components such as perspiration and are capable of preventing the passage of oils and greases through their structure.

The term "heat sealable" is used herein to describe microporous membrane materials which can be sealed together using a hot bar, ultrasonic, or other thermal process sealer to form a bond having a bond strength of at least 0.1 kg/cm width.

The thermally induced phase separated oleophobic, hydrophobic, moisture permeable, air permeable, heat sealable, microporous membrane materials useful in the present invention can, for example, be made by the following steps: (a) melt blending into a homogeneous blend, a mixture comprising about 40 to about 80 parts by weight of a crystallizable olefin polymer, about 20 to 60 parts by weight of a processing compound which will dissolve the polymer at the polymer's melting temperature but which will also phase separate from the polymer on cooling to a temperature at or below the crystallization temperature of the polymer, and 1 to 5 parts by weight of the fluorochemical oxazolidinone or fluorochemical aminoalcohol compound; (b) forming a film from the melt blended mixture; (c) cooling the film to a temperature at which phase separation occurs between the processing compound and the polymer, thereby creating a phase separated film comprising an aggregate of a first phase comprising particles of olefin polymer in a second phase comprising the processing compound and the fluorochemical oxazolidinone or fluorochemical aminoalcohol compound, with adjacent olefin polymer particles being distinct but having a plurality of zones of continuity; and (d) stretching the phase separated film in at least one direction to separate adjacent particles of olefin polymer from one another to provide a network of inter-connected micropores and to permanently attenuate the olefin polymer in the zones of continuity to form fibrils. Optionally, other materials such as dyes, pigments, antistatic agents and nucleating agent may also be added in step (a). Such methods are described, for example, in U.S. Pat. No. 4,539,256 (Shipman), U.S. Pat. No. 4,726,989 (Mrozinski), U.S. Pat. No. 4,863,792 (Mrozinski) and U.S. Pat. No. 5,120,594 (Mrozinski), which are incorporated herein by reference.

The preferred phase separated films typically are solid and generally transparent before stretching and comprise an aggregate of a first phase of particles of olefin polymer in a second phase of the processing compound and the fluorochemical oxazolidinone or fluorochemical aminoalcohol compounds. The particles may be described as spherulites and aggregates of spherulites of the olefin polymer, with processing compound and the fluorochemical oxazolidinone or fluorochemical aminoalcohol compounds occupying the space between particles. Adjacent particles of polymer are distinct, but they have a plurality of zones of continuity. That is, the polymer particles are generally substantially, but not totally, surrounded or coated by the processing compound and the fluorochemical oxazolidinone or fluorochemical aminoalcohol compound. There are areas of contact between adjacent polymer particles where there is a continuum of polymer from one particle to the next adjacent particle in such zones of continuity.

On stretching, the polymer particles are pulled apart, permanently attenuating the polymer in zones of continuity, thereby forming the fibrils and creating minute voids between coated particles which results in a network of interconnected open micropores. Such permanent attenuation also renders the article permanently translucent. On stretching, the processing compound and the fluorochemical oxazolidinone or fluorochemical aminoalcohol compound remain coated on or substantially surrounding the surfaces of the resultant fibril/particle matrix such that the micropores remain open and unfilled. The degree of coating depends on several factors, including, but not limited to, the affinity of the compound and the fluorochemical, oxazolidinone or the fluorochemical aminoalcohol compound for the surface of the polymer particle, whether the compound is liquid or solid, and whether stretching dislodges or disrupts the coating. After the stretching operation, substantially all of the particles appear to be connected by fibrils and are usually at least partially coated. The size of the micropores is easily controlled by varying the degree of stretching, the amount of processing compound employed, melt-quench conditions, and heat stabilization procedures. For the most part, the fibrils do not appear to be broken by stretching, but they are permanently stretched beyond their elastic limit so that they do not elastically recover to their original position when the stretching force is released. As used herein, "stretching" means such stretching beyond the elastic limit so as to introduce permanent set or elongation to the microporous membrane material.

The melting and crystallization temperature of an olefin polymer, in the presence of a processing compound, is influenced by both an equilibrium and a dynamic effect. At equilibrium between liquid and crystalline polymer, thermodynamics require that the chemical potentials of the polymer in the two phases be equal. The temperature at which this condition is satisfied is referred to as the melting temperature, which depends upon the composition of the liquid phase. The presence of a diluent, e.g., the processing compound, in the liquid phase will lower the chemical potential of the polymer in that phase. Therefore, a lower melting temperature is required to re-establish the condition of equilibrium, resulting in what is known as a melting temperature depression.

The crystallization temperature and melting temperature are equivalent at equilibrium. However, at non-equilibrium conditions, which are normally the case, the crystallization temperature and melting temperature are dependent on the cooling rate and heating rate, respectively. Consequently, the terms "melting temperature" and "crystallization temperature," when used herein, are intended to include the equilibrium effect of the processing compound as well as the dynamic effect of the rate of heating and cooling.

The thermally induced phase separated microporous membrane materials useful in the present invention preferably have a microporous structure generally characterized by a multiplicity of spaced, i.e., separated from one another, randomly dispersed, non-uniform shaped, equiaxed particles of olefin polymer connected by fibrils which are intimately surrounded by the processing compound and the fluorochemical oxazolidinone or fluorochemical aminoalcohol compound. "Equiaxed" means having approximately equal dimensions in all directions.

Nucleating agents as described in U.S. Pat. No. 4,726,989 (Mrozinski) may also be used in the preparation of the microporous membrane materials useful in the present invention. The use of nucleating agents provides various advantages including lower polymer content and thus higher porosity of the finished article, reduced polymer particle size resulting in more particles and fibrils per unit volume, greater stretchability resulting in longer fibril length, and greatly increased tensile strength of the material.

Other types of microporous membrane useful in the present invention include those prepared from polyolefin resin, an inorganic particulate filler and a fluorochemical compound capable of providing viral barrier properties, the membranes being stretched in at least one direction. U.S. Pat. No. 3,844,865 (Elton) and U.S. Pat. No. 5,317,035 (Jacoby et al.) describe microporous membranes prepared from polyolefin resin or resin blends and filler material and are incorporated herein for that purpose.

Polyolefins useful in the particle-containing microporous membranes include, for example, polypropylene, polyethylene, ethylene-propylene block copolymers, polybutylene, a-olefin polymers, and combinations thereof.

Inorganic particulate fillers which can be used are solid inorganic alkali earth metal salt particles which are nonhygroscopic, light-colored, water insoluble, easily pulverized, finely divided, and have densities below about 3 g/cc and melting points above olefin degradation temperatures. Particularly preferred is calcium carbonate, although other inorganic salts may be used such as, for example, alkaline earth metal carbonates and sulfates, particularly magnesium carbonate, calcium sulfate and barium sulfate.

Crystallizable olefin polymers suitable for use in the preparation of microporous membrane materials useful in the present invention are melt processable under conventional processing conditions. That is, on heating, they will easily soften and/or melt to permit processing in conventional equipment, such as an extruder, to form a sheet, film, tube, filament or hollow fiber. Upon cooling the melt under controlled conditions, suitable polymers spontaneously form geometrically regular and ordered crystalline structures. Preferred crystallizable polymers for use in the present invention have a high degree of crystallinity and also possess a tensile strength of at least about 70 kg/cm$^2$ (1000 psi).

Examples of commercially available suitable crystallizable polyolefins include polypropylene, block copolymers or copolymers of ethylene and propylene, or other copolymers, such as polyethylene, polypropylene and polybutylene copolymers, which can be used singularly or in a mixture.

Materials suitable as processing compounds for blending with the crystallizable polyolefin to make the microporous membrane materials useful in the present invention are liquids or solids which are not solvents for the crystallizable polymer at room temperature. However, at the melt temperature of the crystallizable polymer the compounds become good solvents for the polymer and dissolve it to form a homogeneous solution. The homogeneous solution is extruded through, for example, a film die, and on cooling to or below the crystallization temperature of the crystallizable polymer, the solution phase separates to form a phase separated film. Preferably, these compounds have a boiling point at atmospheric pressure at least as high as the melting temperature of the polymer. However, compounds having lower boiling points may be used in those instances where superatmospheric pressure may be employed to elevate the boiling point of the compound to a temperature at least as high as the melting temperature of the polymer. Generally, suitable compounds have a solubility parameter and a hydrogen bonding parameter within a few units of the values of these same parameters for the polymer.

Some examples of blends of crystalline olefin polymers and processing compounds which are useful in preparing microporous materials in accordance with the present invention include: polypropylene with mineral oil, dioctylphthalate, or mineral spirits; and polyethylene-polypropylene copolymers with mineral oil or mineral spirits. Typical blending ratios are 40 to 80 weight percent polymer and 20 to 60 weight percent processing compound.

A particular combination of polymer and processing compound may include more than one polymer, i.e., a mixture of two or more polymers, e.g., polypropylene and polybutylene, and/or more than one processing compound. Mineral oil and mineral spirits which are substantially non-volatile at ambient conditions are examples of mixtures of processing compounds, since they are typically blends of hydrocarbon liquids. Similarly, blends of liquids and solids may also serve as the processing compound. Hydrocarbons suitable for use include both liquids and solids. The liquids are generally mixtures of various molecular weights and with increasing weight become more viscous, i.e., light to heavy mineral oils having a carbon chain length of at least about 20, and with increasing molecular weight become gels, such as petroleum jelly, and then solids, such as waxes having a carbon chain length of about 36.

Other types of microporous materials can also be useful in the present invention as long as the pore size is sufficiently small and pore size distribution is sufficiently narrow that when the fluorochemical compound is present, the article formed provides viral barrier properties. Such microporous materials include, for example, those formed from polytetrafluoroethylene as described in U.S. Pat. No. 3,953,566 (Gore), U.S. Pat. No. 3,962,153 (Gore) and U.S. Pat. No. 4,096,227 (Gore) and those formed from thermoplastic materials as described in U.S. Pat. No. 5,055,338 (Sheth et al.) and U.S. Pat. No. 4,929,303 (Sheth). Useful thermoplastic materials include polyolefin, nylon, polyester, polyphenylene oxide, polystyrene, polyvinyl chloride, polyvinyl acetate, polyvinyl alcohol, polymethyl-methacrylate, polycarbonate and polysulfone.

While the preferred form of the microporous membrane materials useful in the present invention is a sheet or film form, other article shapes are contemplated and may be formed. For example, the article may be in the form of a tube or filament or hollow fiber. Other shapes which can be made according to the disclosed process are also intended to be within the scope of the invention.

Fluorochemical oxazolidinones suitable for use in preparing microporous materials in accordance with the present invention include those described in U.S. Pat. No. 5,025,052 (Crater et al.) which is incorporated herein by reference.

Fluorochemical aminoalcohol compounds suitable for use in preparing microporous materials in accordance with the present invention include, for example, those disclosed in U.S. Pat. No. 3,870,748 (Katsushima et al.), U.S. Pat. No. 4,084,059 (Katsushima et al.) which are incorporated by reference herein and Plenkiewicz et al., "Synthetic Utility of 3-(Perfluoro-1,1-Dimethyl-1-Propene. Part II. Synthesis of New 2-Hydroxy-3-(Perfluoroalkyl)Propyl-Amines", *Journal of Fluorine Chemistry*, vol. 45, pp 389–400 (1989). The fluorochemical oxazolidinones and aminoalcohol compounds useful in the present invention preferably contain at least about 20 weight percent fluorine, more preferably at least about 30 weight percent fluorine.

These oxazolidinone and aminoalcohol compounds are preferably normally blended in the polymer/processing compound mixture in the proportion of 1 to 5 weight percent. More preferably the fluorochemical oxazolidinone and aminoalcohol compounds are added to the polymer/processing compound mixture in the proportion of 1 to 2 weight percent. Fluorochemical oxazolidinone and aminoalcohol compounds can be added to the membranes of the present invention in amounts greater than 5 weight percent (i.e. 10 weight percent), but additions in excess of about 2 weight percent typically do not show any performance advantages.

Certain conventional additive materials may also be added to the microporous material in limited quantities. Additive levels should be chosen so as not to interfere with the formation of the microporous membrane material or to result in unwanted exuding of the additive. Such additives may include, for example, dyes, pigments, plasticizers, UV absorbers, antioxidants, bacteriostats, fungicides, ionizing radiation resistant additives, and the like. Additive levels should typically be less than about 10% of the weight of the polymer component, and preferably less than about 5% by weight.

The microporous membranes used in the surgical gowns and drapes of the invention may also be laminated or layered with other porous materials such as woven cloth, non-woven fabric such as non-woven scrim, or foam material. The use of such additional materials should preferably not affect prevention of viral pathogen transmission or porosity.

The articles provided by the present invention include surgical gowns, drapes, masks, gloves, sterile wraps, wound dressings and waste disposal bags, and descriptions of such articles are found, for example, in U.S. Pat. No. 3,856,005 (Sislian); U.S. Pat. No. 4,976,274 (Hanssen); U.S. Pat. No. 4,845,779 (Wheeler et al.); U.S. Pat. No. 3,911,499 (Benevento et al.); U.S. Pat. No. 4,920,960 (Hubbard et al.); U.S. Pat. No. 4,419,993 (Petersen); U.S. Pat. No. 3,426,754 (Bierenbaum et al.); U.S. Pat. No. 4,515,841 (Dyke); UK Application No. 2,232,905A (Woodcock).

In the following non-limiting examples, all parts and percentages are by weight unless otherwise indicated. In evaluating the materials of the invention and the comparative materials, the following test methods are used.

Porosity

Porosity is measured according to ASTM-D726-58 Method A and is reported in Gurley seconds/50 cc.

Bubble Point

Bubble point values represent the largest effective pore size measured in microns according to ASTM-F-316-80 and is reported in microns.

Moisture Vapor Transmission Rate (MVTR)

Moisture vapor transmission rates (MVTR) were made using ASTM-E96-80 Upright Water Method, low humidity on one side and high humidity on the other. The test chamber conditions were 38° C. and 20% relative humidity. Results are reported in $g/m^2/24$ hr.

Sweat Contamination Resistance

Resistance to sweat contamination was measured according to MIL-C-44187B, Mar. 31, 1988, test method 4.5.7 with water permeability being determined by Fed. Test Method Std. No. 191A, and is reported as being resistant or not resistant, i.e. pass or fail.

Resistance to Viral Penetration by a Blood-Borne Pathogen

To determine a membrane's viral barrier property as in a surgical gown application, ASTM Test Method ES 22-1992 was followed. Basically, this test indicates whether a virus-containing liquid penetrates the test material. A test pressure of 13.8 kPa (2 psi) is applied through the liquid to the test material. The non-liquid-containing side of the test material is then swabbed and the swabbed exudate is cultured for 24 hours. The number of viruses is then counted. Three samples are tested. The test material has distinguishable viral barrier properties if the number of viruses is less than 100 for each sample tested. However, the number of viruses is preferably less than about 10, more preferably zero for each sample tested.

Viral Penetration When Membrane is Stretched

To determine to what degree a membrane can be stretched without affecting the viral barrier property, the following procedure was used. Prior to applying the pressure to the liquid when using the previously described test method (Resistance to Viral Penetration) a one-inch (2.54 cm) line was drawn on the membrane test sample. Then, the pressure was applied to the membrane. While under pressure, the drawn line was re-measured (including the curvature) while applying the pressure. The % stretch was calculated by the following formula:

$$\frac{\text{(Length Under Pressure)} - \text{(Original Length, 1.0'')}}{\text{(Original Length)}} \times 100\% = \% \text{ Stretch}$$

Resistance to Viral Penetration After Sweat Contamination

To determine viral penetration after sweat contamination, membrane samples are exposed to synthetic perspiration according to MIL-C-44187B, Mar. 31, 1988, test method 4.5.6, and then tested for viral penetration using ASTM Test Method ES 22-1992. Using MIL-C-44187B, synthetic sweat was applied to both sides of the membrane and a test pressure of 27.6 kPa (4 psi) was applied for 16 hours. Following this exposure to synthetic sweat, the membrane was tested for resistance to viral penetration by a blood-borne pathogen using ASTM Test Method ES 22-1992. The number of viruses is then counted. Three samples are tested. The test material has distinguishable viral barrier properties if the number of viruses is less than 100 for each sample tested. However, the number of viruses is preferably less than about 10, more preferably zero for each sample tested.

EXAMPLES

OXAZOLIDINONE PREPARATION

The fluorochemical oxazolidinone (FCO) used to prepare the microporous membrane materials in the following examples was similar to that described in U.S. Pat. No. 5,025,052 (Crater et al.) Example 1, except that the alcohol and isocyanate reactants used to prepare the oxazolidinone were $C_8F_{17}SO_2N(CH_3)CH_2CH(CH_2Cl)OH$ and $OCNC_{18}H_{37}$, respectively.

Example 1

A 0.08 mm thick sheet of microporous membrane material was prepared using a thermally induced phase separation technique combining about 64.7 parts polypropylene (PP) having a melt flow index of 0.8 dg/min ASTM 1238 (available from Himont Incorporated, Wilmington, Del. under the trade designation PRO-FAX 6723), about 0.3 parts fluorocarbon oxazolidinone (FCO) compound, and about 35 parts mineral oil (MO), (available from AMOCO Oil Company under the trade designation AMOCO White Mineral Oil #31 USP Grade). The PP/FCO/MO composition was melt extruded on a twin screw extruder operated at a decreasing temperature profile of 260 to 193° C. through a slip gap sheeting die having an orifice of 35.6×0.05 cm and quenched in a water bath maintained at 53° C. The membrane was continuously width stretched or oriented (cross direction) in a tenter oven to a 1.6:1 stretch ratio at 83° C. and heat annealed at 121° C. Membrane characterization data and barrier results are reported in Table I.

Example 2

A 0.06 mm thick sheet of microporous membrane material was prepared using the same materials and process as Example 1, except the materials ratio was 49.5/5.5/45.0, PP/FCO/MO, stretching was at a continuous length direction stretch ratio of 1.25:1 at 50° C. followed by a continuous width direction stretch ratio of 1.75:1 at 83° C., and heat annealing was at 121° C. Membrane characterization data and barrier results are reported in Table I.

Example 3

A 0.05 mm thick sheet of microporous material was prepared using the same materials and process as Example 1, except the materials ratio was 63.7/1.3/35, PP/FCO/MO, stretching was carried out at a continuous length direction stretch ratio of 1.25:1 at 50° C. and a width direction stretch ratio of 2.25:1 at 83° C. and heat annealing was at 121° C. Membrane characterization data and barrier results are reported in Table I.

Example 4

A 0.04 mm thick sheet of microporous membrane material was prepared using the same materials and process as Example 1, except a blue pigment in polypropylene (available from PMS Consolidated, Somerset, N.J. under the trade designation BLUE P293C) was added to color the existing material. The blend ratio of materials was 63.7/1.3/2.0/33.0, PP/FCO/BLUE/MO. In the process, a molten blend maintained at 205° C. was cast from a slip gap sheeting die with a 38.1×0.05 cm orifice onto a smooth steel casting wheel maintained at 66° C. The membrane was then continuously length direction stretched at a ratio of 1.75:1 and continuously width direction stretched 2:1 at 93° C. and heat annealed at 130° C. This membrane was subjected to 20.7 kPa (3 psi) within the Viral Penetration Test and the % stretch was calculated to be 25%. Membrane characteristics and barrier results are reported in Table I.

Examples 5 and 6

A 0.03 mm thick sheet of microporous membrane material was prepared for lamination to a polypropylene spun-bonded nonwoven using the same materials as Example 4, except a polybutylene (PB) copolymer (available from Shell Chemical Company under the trade designation PP 8510) was added to make a blend ratio of 61.8/1.3/2.0/5.0/30, PP/FCO/BLUE/PB/MO.

This composition was melt extruded through a circular blown film die having a diameter of 30.5 cm and an orifice of 0.05 cm to form a 2 mil film with a lay flat width of 91 cm. The membrane was continuously length stretched to a 1.6:1 stretch ratio at 38° C. and heat annealed at 119° C. The membrane was then thermally laminated to a 1.0 ounce polypropylene spunbond nonwoven (trademarked "Celestra", supplied by Fiberweb). The laminating process included running an assembly consisting essentially of the membrane and nonwoven between a smooth roll and a heated point-bonding roll (approximately 15 percent point contact) such that the heated point bonding roll applied heat exogenously at spaced-apart points to create a thermal point bonded, viral barrier laminate. The heat roll was set at 270° F. The pressure applied to the materials was approximately 250 pounds per lineal inch. The characterization data and viral barrier results of this membrane/nonwoven laminate, representing Example 5, are reported in Table I.

The same membrane was also adhesively bonded to a similar 1.0 ounce PP spunbonded nonwoven. The adhesive used was a polybutylene resin made by Shell, identified as DP9891D Duraflex, spray applied in a random pattern. The adhesive weight applied was approximately 2 g/m². The characterization data and viral barrier results of this membrane/nonwoven laminate, representing Example 6, are reported in Table 1.

Example 7

The same membrane described in Example 2 was challenged at 20.7 kPa (3 psi) test pressure during the Resistance to Viral Penetration Test, as described above, rather than the standard 13.8 kPa (2 psi) test pressure. At this higher pressure, the % stretch was calculated to be 20%. Membrane characterization and barrier results are reported in Table I.

Comparative Example C1

A 0.04 mm thick sheet of microporous membrane material was prepared using the same materials, ratio and process as Example 1, except the FCO was omitted from the formulation, and the PP/MO blend was cast as a blown film using the same conditions as in Examples 5 and 6. Then the film was length direction stretched to a 1.85:1 stretch ratio at 38° C. and heat annealed at 119° C. Membrane characterization and barrier results are reported in Table I.

TABLE I

| Ex. No. | CALIPER (mm) | % FCO | POROSITY (sec/50 cc) | BUBBLE POINT ($\mu$m) | MVTR (g/m$^2$/ 24 hr) | VIRAL RESIST (Pass/Fail) | RESISTANCE TO SWEAT CONTAMINATION Before/After |
|---|---|---|---|---|---|---|---|
| 1 | 0.08 | 0.3 | 60 | 0.52 | 8070 | 0-0-0 | P/P |
| 2 | 0.06 | 5.5 | 184 | 0.26 | 7489 | 0-0-0 | P/P |
| 3 | 0.05 | 1.3 | 382 | 0.15 | 7008 | 0-0-0 | P/P |
| 4 | 0.04 | 1.3 | 200 | 0.28 | 6954 | 0-0-0* | P/P |
| 5 | 0.03 | 1.3 | 221 | 0.40 | — | 0-0-0* | — |
| 6 | 0.03 | 1.3 | 295 | 0.32 | 5151 | 0-0-0 | — |
| 7 | 0.06 | 5.5 | 184 | 0.26 | 7489 | 0-0-0* | P/P |
| C1 | 0.04 | 0.0 | 233 | 0.33 | 6490 | >600 >600 >600 | P/F |

*Example 4 and Example 7 passed the Resistance to Viral Penetration Test at 20.7 kPa (3 psi) (other membrane examples were tested at 13.8 kPa (2 psi)), even though the 20.7 kpa (3 psi) stretched Example 4 by 25% and Example 7 by 20%.

Example 1 is especially significant because of the large pore size of the membrane and the small amount of FCO utilized to render it liquid repellent.

Example 8

A 0.03 mm (1.2 mil) thick sheet of microporous membrane material was prepared using the same materials and process as Example 4, except blue pigmented polypropylene (BPP) designated BN-AP, available from Hoechst-Celanese was added and the materials ratio was 58.5/4.3/1.5/35.7, PP/BPP/FCO/MO, stretching was at a continuous length direction stretch ratio of 1.8:1 at 50° C. followed by a continuous width direction stretch ratio of 1.6:1 at 83° C. and heat annealing was at 121° C.

Membrane characterization data and barrier results were determined to be as follows: porosity—158.3 sec/50 cc, bubble point—0.25 $\mu$m, MVTR—7722, resistance to viral penetration—0—0—0, resistance to sweat contamination—pass, resistance to viral penetration after sweat contamination—0—0—0.

Example 9

N-methyl-N-glycidyl-perfluorooctanesulfonamide ("epoxide A") was prepared by placing 450 grams N-methyl-perfluorooctanesulfonamide ("amide A") in a two-liter three-necked round-bottom flask and heating to 80° C., 101 grams epichlorohydrin was then added followed by 91 grams methanol. The temperature was reduced to 65° C. before 30 grams 25 wt % sodium methoxide in methanol solution was slowly added keeping the temperature below 70° C. 60 grams 50 wt % aqueous sodium hydroxide solution was slowly added keeping the temperature below 70° C. After addition the reaction was stirred at 65° C. overnight. Water-aspirator vacuum was applied to the flask and excess methanol and epichlorohydrin were removed. 450 grams water was then added to the flask with stirring at 65° to wash the product. The water was decanted after allowing the product to settle. This washing step was repeated a second time. Vacuum was applied to 20 mm Hg and the temperature of the flask was raised to 90° C. to remove volatile materials.

In a one-liter, three-necked round bottom flask fitted with a mechanical stirrer, condenser, gas inlet tube, thermometer, and electric heating mantel were placed 250.0 g (0.44 moles) of epoxide A and 250 mL toluene solvent under a nitrogen blanket. To this stirred solution heated to 60° C. was added 118.4 g (0.44 moles) octadecylamine in small portions over a 15 minute period. After addition of the amine was complete the temperature of the reaction was raised to 115° C. and the reaction was stirred for 12 hours at this temperature until all of the starting epoxide had been converted to aminoalcohol as determined by gas chromatographic analysis. The reaction mixture was cooled to a temperature of about 25° C. and excess toluene solvent was removed under vacuum with a rotary evaporator. Infrared, proton NMR, and mass spectroscopic analysis confirmed the product to be a fluorochemical aminoalcohol of this invention having the structure $C_8F_{17}$—$SO_2N(CH_3)CH_2$—$CH(OH)CH_2NH$—$C_{18}H_{37}$.

A 0.035 mm thick sheet of microporous membrane material was prepared using 59.3 weight percent of the polypropylene (PP) and 35.5 weight percent of the mineral oil (MO) used in Example 1, 3.7 weight percent blue pigmented polypropylene (BPP) designated BN-AP, available from Hoechst-Celanese, and the 1.5 weight percent of the fluorocarbon aminoalcohol prepared as described above. These materials were processed on a 40 mm twin screw extruder using a decreasing temperature profile of 270° C. to 205° C. through a slip gap sheeting die with a 38.1×0.05 cm orifice onto a smooth chill roll maintained at 63° C. The resulting membrane was biaxially oriented 1.9:1×1.6:1 at 94° C. and heat annealed at 130° C. Membrane characterization data and barrier results were determined to be as follows: porosity—131 sec/50 cc; bubble point—0.22 $\mu$m; and resistance to viral penetration—0–6–0.

Example 10

A 0.076 mm thick sheet of microporous membrane material was prepared using 58.9 weight percent of the polypropylene and 36.7 weight percent of the mineral oil used in Example 1, 3.1 weight percent blue pigmented polypropylene designated BN-AP, available from Hoechst-Celanese, and 1.5 weight percent of the fluorocarbon aminoalcohol prepared as described above. These materials were processed on a 40 mm twin screw extruder using a decreasing temperature profile of 270° C. to 177° C. through a slip gap sheeting die with a 38.1×0.05 cm orifice onto a pyramid 100 patterned casting wheel maintained at 38° C. The resulting membrane was oriented 1.9:1 at 60° C. and heat annealed at 94° C. Membrane characterization data and barrier results were determined to be as follows: porosity—754 sec/50 cc; bubble point—0.15 μm; and resistance to viral penetration—0—0—0.

Examples 11–14 and Comparative Example C2

For Examples 11–14, a hydrophilic microporous nylon membrane (NYLAFLO, 0.20 μm pore size, available from Baxter Scientific Products) was dipped in a solution containing 2.0 weight percent fluorochemical composition until wet out, about 10 seconds. The fluorochemical compositions were: Example 11—fluorochemical oxazolidinone in trichloroethane; Example 12—TEFLON 1600 (amorphous fluoropolymer available from DuPont Co.) in FLUORINERT-75 (fluorochemical liquid available from 3M Company); Example 13—ZONYL (fluoroacrylate monomer available from DuPont Co.) polymerized in situ as described in U.S. Pat. No. 5,156,780 and Example 14—fluorochemical piperazine in toluene solvent. The membranes were then dried to remove solvent. The treated membranes were tested for porosity and resistance to viral penetration. In Comparative Example C2, an untreated NYLAFLO microporous membrane was tested for porosity and resistance to viral penetration. The results are set forth in Table II.

TABLE II

| Example | Porosity (sec/50 cc) | Viral Resistance (Pass/Fail) |
|---|---|---|
| C2 | 25 | >600->600->600 |
| 11 | 222 | 0-0-0 |
| 12 | 27 | 0-0-0 |
| 13 | 37 | 0-0-0 |
| 14 | 616 | 0-147-1 |

Examples 15–16 and Comparative Example C3

For Examples 15–16, a hydrophilic acrylic microporous membrane (VERSAPOR-450, 0.45 μm pore size, available from Baxter Scientific Products) was dipped in a solution containing 2.0 weight percent fluorochemical composition until wet out, about 10 seconds. The fluorochemical compositions were: Example 15—FC-3537 (a fluoroacrylate polymer, available from 3M Company) in ethyl acetate; and Example 16—N-methylperfluorooctane-sulfonamidoethyl stearate in toluene. The membranes were then dried to remove solvent. The treated membranes were tested for porosity and resistance to viral penetration. In Comparative Example C3, an untreated VERSAPOR-450 microporous membrane was tested for porosity and resistance to viral penetration. The results are set forth in Table III.

TABLE III

| Example | Porosity (sec/50 cc) | Viral Resistance (Pass/Fail) |
|---|---|---|
| C3 | 7.5 | >600->600->600 |
| 15 | 20 | 0-0-0 |
| 16 | 65 | 14-1-0 |

The fluorochemical piperazine used in Example 14 was prepared as follows:

To a 1-L round bottom flask, equipped with a magnetic stir bar, was added 51.7 g anhydrous piperazine and 200 mL methylene chloride. With slight cooling of the reaction vessel with a cold water bath, 75.3 g perfluorooctanesulfonyl fluoride was added over a 5–10 minute period. The resulting yellow solution was allowed to stir for an additional 2 hrs, then ice chips were added followed by addition of ice cold deionized water. The layers were separated and the organic layer was washed with two additional portions of deionized water. After drying over anhydrous sodium sulfate, the solvent was removed under reduced pressure. Distillation (0.65–0.70 mm, 140–142° C., first cut, was discarded) yielded 52.4 g N-(perfluorooctanesulfonyl) piperazine.

To a 500 mL round bottom flask equipped with a magnetic stir bar and a nitrogen inlet was added 25.6 g of the N-(perfluorooctanesulfonyl) piperazine and 150 mL methylene chloride. A solution of 13.6 g stearoyl chloride in 50 mL methylene chloride was added dropwise to the reaction vessel. After addition was complete, slight heating was applied to ensure complete reaction. After stirring overnight, the solvent was removed under reduced pressure. The residue was taken up in chloroform and washed with three portions of deionized water and one portion of saturated aqueous sodium chloride solution. After drying over anhydrous sodium sulfate, the solvent was removed under reduced pressure, to yield a compound of the formula

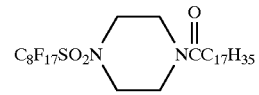

Example 17 and Comparative Example C4

In Comparative Example C4, a microporous membrane was prepared according to U.S. Pat. No. 5,317,035 by melt blending 50 weight percent ethylene/propylene copolymer (HIFAX RA-061™, available from Himont, Inc., 35 weight percent of a polypropylene/calcuim carbonate blend (PF-85F™ containing 60 weight percent polypropylene having a melt flow rate of 4.0 and 40 weight percent calcium carbonate, mean particle size 0.8 microns, available from A. Schulman, Inc.) and 15 weight percent low molecular weight polypropylene resin (PROFLOW™-1000, melt viscosity 137 poise measured at 136 sec-1 and 190° C., available from Polyvisions, Inc.) using a 25 mm twin screw extruder maintained at a decreasing temperature profile from 249° C. to 215° C. at a throughput rate of 1.8 kg/hr through a sheeting die with a 30.5 cm×0.508 mm orifice onto a steel casting wheel maintained at 93° C. to form a cast film 0.127 mm thick. The film was stretched 2×2 on a T.M. LONG™ film stretcher at 91° C. The film was heat set at 82° C. for 10 minutes.

In Example 17, a microporous membrane was prepared and oriented in a manner similar to that of Comparative Example C4 except 1.5 weight percent FCO was added to the melt blend of Comparative Example C4 based on total film weight.

Samples of membrane of each of Example 17 and Comparative Example C4 were tested for porosity, bubble point pore size, and resistance to viral penetration. The results are set forth in Table IV.

TABLE IV

| Example | Bubble Point (μm) | Porosity (sec/50 cc) | Viral Resistance (Pass/Fail) |
|---------|-------------------|----------------------|------------------------------|
| C4      | 1.01              | 111                  | 0-20-300                     |
| 17      | 0.83              | 150                  | 0-0-0                        |

Example 18

A microporous membrane was prepared by melt blending 89.6 weight percent of a 60:40 weight ratio blend of linear low density polyethylene:calcium carbonate (FLP 697-01, available from A. Shulman, Inc.), 9.9 weight percent linear low density polyethylene (ASPUN™ XU61800.31, melt flow index 150, available from Dow Chemical Company) and 1.5 weight percent FCO using a 25 mm twin extruder operated at 1.8 kg/hr and 254° C. and cast onto a smooth casting wheel maintained at 93° C. to form a 0.13 mm thick membrane. The resultant membrane was stretched 1.5×2.5 at 100° C. and was heat set at 79° C. for 15 minutes. The results of membrane testing were:

Porosity: 90 sec/50 cc

Bubble Point: 0.22 μm

Thickness: 0.065 mm

Viral Resistance: 0—0–15

The various modifications and alterations of this invention will be apparent to those skilled in the art without departing from the scope and spirit of this invention and this invention should not be restricted to that set forth herein for illustrative purposes.

What we claim is:

1. A process of thermally laminating a viral barrier microporous membrane to a nonwoven web comprising calendaring an assembly consisting essentially of the microporous membrane and the nonwoven web between a smooth roll and a heated point bonding roll such that the heated point bonding roll applies heat exogenously at spaced-apart points to create a thermal point bonded, viral barrier laminate having viral properties, wherein the viral barrier laminate permits less than 100 viruses to pass according to ASTM Method ES 22-1992, wherein the microporous membrane comprises a thermoplastic polymer and a water- and oil-repellent fluorochemical compound that forms a microporous membrane with oleophobic and hydrophobic properties and further wherein the microporous membrane of the laminate comprises interconnected open and unfilled pores.

2. The process of claim 1 wherein a moisture vapor transmission rate for the viral barrier laminate comprises at least 1000 g/m²/24 hours.

3. The process of claim 1 wherein air permeability expressed as Gurley porosity of the viral barrier laminate comprises approximately 200 seconds/50 cc.

4. The process of claim 1 wherein the nonwoven web comprises a sponbond nonwoven polypropylene web.

5. The process of claim 1 wherein the viral barrier laminate permits less than 10 viruses to pass according to ASTM Test Method ES 22-1992.

6. The process of claim 1 wherein the viral barrier laminate permits no viruses to pass according to ASTM Test Method ES 22-1992.

7. The process of claim 1 further including the step of constructing an article from the viral barrier composite.

8. The process of claim 1 further including the step of constructing a surgical gown from the viral barrier composite.

9. A process of thermally laminating a viral barrier microporous membrane to a nonwoven web comprising calendaring an assembly comprising the microporous membrane and the nonwoven web between a smooth roll and a heated point bonding roll such that the heated point bonding roll applies heat exogenously at spaced-apart points to create a thermal point bonded, viral barrier laminate, wherein the viral barrier laminate permits less than 100 viruses to pass according to ASTM Method ES 22-1992, wherein the microporous membrane comprises a thermoplastic polymer and a water- and oil-repellent fluorochemical compound that forms a microporous membrane with oleophobic and hydrophobic properties and further wherein the microporous membrane of the laminate comprises interconnected open and unfilled pores.

* * * * *